United States Patent [19]

Weithmann et al.

[11] Patent Number: 4,975,432
[45] Date of Patent: Dec. 4, 1990

[54] METHOD OF USING PENTOXIFYLLINE FOR TREATING INFLAMMATION

[75] Inventors: Klaus U. Weithmann, Hofheim am Taunus; Dirk Seiffge, Münzenberg, both of Fed. Rep. of Germany

[73] Assignee: Hoechst Aktiengesellschaft, Frankfurt am Main, Fed. Rep. of Germany

[21] Appl. No.: 390,076

[22] Filed: Aug. 7, 1989

Related U.S. Application Data

[63] Continuation of Ser. No. 219,809, Jul. 14, 1988, Pat. No. 4,880,791, which is a continuation of Ser. No. 756,673, Jul. 19, 1985, abandoned.

[30] Foreign Application Priority Data

Jul. 21, 1984 [DE] Fed. Rep. of Germany ....... 3426961
Mar. 7, 1985 [DE] Fed. Rep. of Germany ....... 3508097

[51] Int. Cl.$^5$ .................... A01N 43/90; A61K 31/52
[52] U.S. Cl. .................................... 514/261; 514/262
[58] Field of Search .......................... 514/261, 262

[56] References Cited

U.S. PATENT DOCUMENTS

4,558,051 12/1985 Sunshine et al. ................. 514/657
4,853,386  8/1989 Friebe et al. ...................... 514/261
4,880,791 11/1989 Weithmann et al. ............. 514/161

FOREIGN PATENT DOCUMENTS

69958 1/1983 European Pat. Off. .

OTHER PUBLICATIONS

Sakurai et al., Abstract from the Japanese Journal of Pharmacology, vol. 33, 1983.
Remien et al., Abstract from the Archives of Pharmacology, vol. 293, 1976.
Rote Liste, 1987, No. 36056.
Gallenkamper et al., Br. J. Pharmac., 81, 1984, pp. 575–581.

Primary Examiner—Nathan M. Nutter
Attorney, Agent, or Firm—Finnegan, Henderson, Farabow, Garrett, and Dunner

[57] ABSTRACT

A combination product containing (A) on the one hand a xanthine derivative of the formula

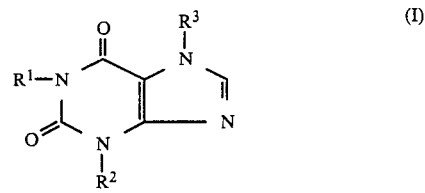

in which one of the radicals $R^1$ and $R^3$ represents a straight-chain alkyl, $\omega$-1)-oxoalkyl or ($\omega$-1)-hydroxyalkyl group having 3 to 8 carbon atoms, and the two other radicals $R^2$ and $R^3$, or $R^1$ and $R^2$ represent straight-chain or branched alkyl groups having 1 to 8 carbon atoms in the position of $R^1$ and $R^3$ and 1 to 4 carbon atoms in the position of $R^2$, the maximum total of carbon atoms in these two alkyl substituents being 10, or of the formula

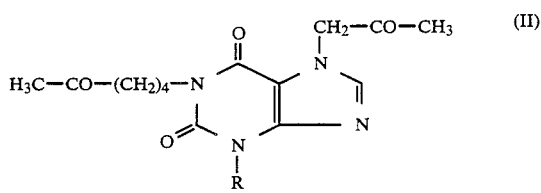

in which R represents an alkyl radical having 1 to 4 carbon atoms, or prodrug forms of the oxoalkylxanthines of the formula I and II or of the hydroxylalkylxanthine of the formula I, or its metabolites, and (B) on the other hand O-acetylsalicylic acid or its pharmacologically tolerated salts, (C) with or without a pharmaceutical vehicle, for sequential administration in the treatment of diseases caused or characterized by impaired constituents of blood, in particular platelets or erythrocytes, but also leukocytes, in such a manner that component (A) is released first, and its use in human and veterinary medicine.

1 Claim, No Drawings

METHOD OF USING PENTOXIFYLLINE FOR TREATING INFLAMMATION

This is a continuation of application Ser. No. 07/219,809, filed July 14, 1988 and now U.S. Pat. No. 4,880,491 which was a Rule 62 Continuation Application of Ser. No. 06/756,673 filed July 19, 1985 and now abandoned.

It is known that 1-(5-oxohexyl)-3,7-dimethylxanthine (pentoxifylline) is used as a pharmaceutical agent for the improvement of the flow properties of blood. The supposed cause of this is (Deutsche mediz, Wochenschrift 107 (1982), 1674) that the viscous stress of the blood decreases because the deformability of the erythrocytes is improved by treatment with pentoxifylline. Moreover, the in vitro aggregation of platelets can be inhibited by pentoxifylline, but only at concentrations which are above those used in medicinal treatment (IRCS (Med. Sci.) 8 (1980) 293, Thrombos, Haemostas, 46 (1981) 272).

In addition, it has been reported that, with pentoxifylline, the release of a substance having antiaggregatory activity from rat aortas ex vivo can be increased by treatment of the animals with pentoxifylline. It is likewise known that the release of the substance having antiaggregatory activity, presumably prostacyclin, thus stimulated can be suppressed by treatment of the rats with acetylasalicyclic acid (Vasa 10 (1981) 249). Our own continuing experiments have confirmed this (see below).

O-Acetylsalicylic acid is known to be an inhibitor of the aggregation of human blood platelets (for example Br. J. clin. Pharmac. 7 (1979) 283), and it has been reported that it may sow valuable therapeutic effects in terms of the prevention of thromboses and strokes 1073. N. Engl. J. Med. 299 (1978). The mechanism of action has been reported to be that acetylsalicylic acid inhibits the enzyme cyclooxygenase, which is localized in the blood platelets (J. Clin. Invest. 56 (1975) 624), and the biosynthesis of thromboxane $A_2$, which promotes the aggregation, is inhibited. However, acetylsalicylic acid is also able to inhibit the cyclooxygenase located in the vessel wall and thus the synthesis of prostacyclin, which inhibits the aggregation. However, since the inhibition of vascular cyclooxygenase is found only at higher doses of acetylsalicylic acid (Pharmacol. Research Commun. 10 (1978) 759), consequently the recommendation is that an antithrombotic effect be achieved with low doses of acetylsalicylic acid (Lancet, iii (1979) 1213, Prostaglandins and Medicine 4 (1980) 439). However, there is also a report that the antithrombotic effect of acetylsalicylic acid increases with increasing doses, and that an optimal effect is achieved under conditions in which there is substantial inhibition of the biosynthesis of both prostacyclin and thromboxane (Prostaglandins, Leukotrienes and Medicine 12 (1983) 235).

The summation of the favorable effect of acetylsalicylic acid on the one hand, and that of the xanthine derivative 7-(2-diethylaminoethyl)theophylline on the other hand, by preparation of the acid-base adduct of the two individual substances and its use in medicine has also already been disclosed (GB Laid-Open Application No. 2 096 138). In addition, the effect of combined, simultaneous administration of pentoxifylline and acetylsalicylic acid on the survival time of platelets in patients with artificial heart valves has been disclosed (Singapore Med. Journal 20 Suppl. 1 (1979) 30).

It has now been found that administration, successively with a time interval, of (A) xanthine derivatives or their active metabolites on the one hand, and (B) acetylsalicylic acid or its pharmacologically tolerated salts on the other hand, in a particular sequence, makes possible an extremely great improvement in the treatment of disorders which are caused or characterized by impaired constituents of blood, in particular platelets or erythrocytes, but also leukocytes. The sequential administration of the xanthine derivatives, in particular pentoxifylline, followed by the administration of acetylsalicylic acid or of its salt, only after until 10 minutes to 4 hours have elapsed, leads to much greater effects than when there is simultaneous administration of the combination of the two individual substances, in which case there is in fact a reduction in this effect. This is all the more surprising since the simultaneous administration of xanthine derivatives, such as pentoxifylline, and acetylsalicylic acid leads only to such antithrombotic and antiaggregatory effects as would have been obtained on administration of acetylsalicylic acid alone (see below, Tables 1 and 2).

Thus the invention relates to combination products containing (A) xanthine derivatives of the formula (I) or (II), (see Patent claim 1) or prodrugs of oxoalkyl- or hydroxyalkylxanthines, or their active metabolites, and (B) O-acetylsalicylic acid or its pharmacoolgically tolerated salts, with or without (C) a pharmaceutical vehicle, for sequential administration in the treatment of disorders caused or characterized by impaired constituents of blood, in particular platelets or erythrocytes, but also leukocytes, in such a manner that component (A) is released first. In other words, the agents according to the invention are suitable, because of their superadditive effects, for antithrombotic, bloodflow-promoting, antiinflammatory, analgesic, antiaggregatory and cytostatic treatment or prophylaxis. Thus the invention also relates to the use of (A) xanthine derivatives of the formula I or II, or of prodrug forms of the oxoalkylxanthines of the formulae I and II, or of the hydroxyalkylxanthines of the formula I, or of their metabolites, and (B) O-acetylsalicylic acid or its pharmacologically tolerated salts, (C) with or without pharmaceutical vehicles for the preparation of agents which bring about sequential release, in such a manner that component (A) is released first, for disorders which are caused by impaired constituents of blood. The invention furthermore relates to the preparation of pharmaceutical formulations as claimed in claim 3, and to the use of the agent in human and veterinary medicine. The combination products according to the invention make it possible for the xanthine derivative to be released, i.e. be bioavailable, even before the acetylsalicyclic acid.

It is a particular advantage that, because of the superadditive effect on consecutive administration, the amounts of xanthine derivative and acetylsalicylic acid which are to be administered can be reduced to those amounts which, on administration alone, show only a minimal pharmacological effect so that, at the same time, side effects which are elicited by high doses of these medicaments can be diminished. This is of great importance because it is known that acetylsalicylic acid can, in the customary doses, elicit undesired side effects (for example British Journal of Clinical Pharmacology 1980, 10, Suppl. 2 and International Meeting on Side Effects of Antiinflammatory, Analgesic Drugs, Verona, Sept, 13–15, 1982, Abstracts), such as asthma, allergic urticaria, analgesic nephropathy and peptic ulcers.

Moreover, the xanthine derivatives may show undesired side effects. By means of the combination product according to the invention it is now possible, surprisingly, to reduce drastically the dose of acetylsalicylic acid necessary for humans, as well as the amount of xanthine derivative, so that there is an even greater improvement in the general toxicological tolerability (see below).

Examples of suitable xanthine derivatives are 1,3,7-trisubstituted compounds of the formula I, in which one of the radicals $R^1$ and $R^3$ is a straight-chain alkyl, $(\omega-1)$-oxoalkyl or $(\omega-1)$-hydroxyalkyl group having 3 to 8 carbon atoms, and the two other radicals $R^2$ and $R^3$, or $R^1$ and $R^2$, are straight-chain or branched alkyl groups having 1 to 8 carbon atoms in the position of $R^1$ and $R^3$, and 1 to 4 carbon atoms in the position of $R^2$, the total of the carbon atoms in these two alkyl substituents being a maximum of 10.

In this context, xanthine compounds of the formula I which are preferred are those in which $R^1$ or $R^3$ denotes an alkyl, $(\omega-1)$-oxalkyl or $(\omega-1)$-hydroxyalkyl radical having 5 to 6 carbon atoms, and the two alkyl substituents $R^2$ and $R^3$, or $R^1$ and $R^2$, together comprise 2 to 6 carbon atoms.

Among these compounds, those which are in turn particularly preferred are those which carry a hexyl, 5-oxohexyl or 5-hydroxyhexyl group in the position of $R^1$ or $R^3$. These include, in particular, 1-hexyl-3,7-dimethylxanthine, 1-(5-hydroxyhexyl)-3,7-dimethylxanthine, 1-(5-oxohexyl)-3,7-dimethylxanthine, 1,3-dimethyl-7-(5-hydroxyhexyl)xanthine, 1,3-dimethyl-7-(5-oxohexyl)xanthine, 1-(5-hydroxyhexyl)-3-methyl-7-propylxanthine and 1-(5-oxohexyl)-3-methyl-7-propylxanthine.

Another suitable group of xanthines comprises the compounds of the formula II, in which R represents an alkyl radical having 1to 4 carbon atoms.

It is not necessary for the oxoalkylxanthines of the formulae I and II and the hydroxyalkylxanthines of the formula I to be used per se, it is also possible to use them in the form of a prodrug from which the therapeutically active xanthine compounds having the substituents defined in the formulae I and II can be released only by biotransformation in the body. Examples of those suitable for this purpose are the acetalized oxoalkylxanthines in which the carbonyl group has been replaced by the structural element of the formula (III) (see patent claim 6), and the O-acylated hydroxylalkylxanthines having the structural element of the formula $R^6$—CO—O— (IV) in place of the hydroxyl group, where $R^4$ and $R^5$ each represent an alkyl group having up to 4 carbon atoms, or together represent an ethylene, trimethylene or tetramethylene group, and $R^6$ denotes an alkyl radical having up to 4 carbon atoms, phenyl, substituted phenyl, pyridyl or substituted pyridyl.

Suitable pharmacologically tolerated salts of acetysalicylic acid are those with pharmacologically tolerated metal cations, ammonium, amine cations or quaternary ammonium cations. Those of the alkali metals, such as lithium, sodium and potassium, and of the alkaline earth metals, such as magnesium and calcium, are preferred, although it is also possible to use cationic forms of other metals, such as aluminum, zinc and iron.

Pharmacologically tolerated amine cations are those of primary, secondary or tertiary amines, such as the alkylamines, for example methyl-, dimethyl-, trimethyl-, ethyl-, dibutyl-, triisopropyl-, N-methylhexyl-, benzyl-, β-phenylethylamine, ethylenediamine, diethylenetriamine, piperidine, morpholine, piperazine, mono-, di- and tri-ethanolamine, ethyldiethanolamine, N-butylethanolamine and the like. Other suitable amine salts are the basic amine salts of lysine and of arginine. Examples of suitable pharmacologically tolerated quaternary ammonium cations are tetramethylammonium, tetraethylammonium and benzyltrimethylammonium.

The xanthine derivatives on the one hand, and the acetylsalicylic acid component on the other hand, can also be administered simultaneously to achieve the superadditive effect, but administration in dosage units in a separate form is preferred, even though the components can also be administered in mixtures, in a suitable form, which permit administration consecutively in time. The dosage units can be in the form of solid drug forms, such as capsules (including microcapsules which, in general, do not contain a pharmaceutical vehicle), tablets (including coated tablets and pills), or suppositories, where, when capsules are used, the capsule material assumes the function of the vehicle, and the contents can be in the form of, for example, a powder, gel, emulsion, dispersion or solution. However, it is particularly advantageous and straight-forward to prepare oral and peroral formulations with the two active compounds, which contain the calculated amounts of the active compounds, together with each desired pharmaceutical vehicle, and which are of such a nature that the release of the active compounds takes place sequentially. It is also possible to use an appropriate formulation (suppository) for rectal treatment. Likewise, transdermal and parenteral (intraperitoneal), intravenous, subcutaneous or intramuscular) injection of solution, for example by means of suitable multichamber injection units, is possible.

Combination products of this type can be prepared by customary processes. The sequential release according to the invention (bioavaiability) of the active compounds can be achieved by covering, in a customary manner, for example according to Sucker, Fuchs and Speiser, Pharmazeutische Technologie (pharmaceutical Technology), Stuttgart 1978, page 424, the tablets, pills or granules, which contain as the medicament acetylsalicylic acid or its medically tolerated salts, such as D,L-lysine monoacetylsalicylates, with a coating which contains as the active compound, for example, pentoxifylline, advantageously in combination with swelling agents (muciferous substances), resins, such as polystyrene, or other customary agents promoting tolerability. .The tablets, pills or granules which are used as the core can be prepared by customary processes and can contain vehicles and other customary auxiliaries, such as starch, for example potato, corn or wheat starch, cellulose or its derivatives, in particular microcrystalline cellulose, silica, various sugars, such as lactose, magnesium carbonate and/or calcium phosphates. The coating, which contains, for example, pentoxifylline, can be applied to the core by, for example, the processes customary in pharmaceutical technology, such as compression, immersion or fluidized bed processes, or by drum coating. The coating solution is usually composed of sugar and/or starch syrup, with the addition of gelatine, gum arabic, polyvinylpyrrolidone, synthetic cellulose esters, surface-active substances, plasticizers, pigments and similar additives according to the state of the art.

The sequential release of the active compounds can also be achieved using layered tablets (this term also including eccentric-core tablets), which are likewise described in Sucker et al., Loc. cit., in which the layer which is absorbed more rapidly contains the xanthine, advantageously likewise combined with muciferous substances or other customary agents promoting tolerability. In this drug form, the release of the active compounds can be achieved by differences in the rates of release from the tablet layers owing to the use of suitable and customary auxiliaries, such as those, for example, detailed above. Gradated release of the two active compounds, for example pentoxifylline and acetylsalicylic acid, can also be achieved by the component which contains the acetylsalicylic acid also containing retarding agents, where appropriate also in the form of permeable membranes, such as those based on cellulose or polystyrene resin, or ion exchangers, or being used in the form of microcapsules which are resistant to gastric juice or make possible delayed release. However, the core containing the acetylsalicylic acid can also be provided with a coating, for example composed of polymethacrylic esters (Eudragit ®) which makes possible delayed release.

All of the customary flow-regulating agents, lubricating agent or lubricants, such as magnesium stearate, and mold-release agents can be used for the preparation of the drug forms.

The ratio by weight of the acetylsalicylic acid to the xanthine derivatives, such as pentooxifylline, can vary within wide limits. The exact ratio which is to be used for a particular combination can readily be determined using the experimental procedures described below. In general, the proportion by weight of xanthine derivatives, for example pentoxifylline, related to one part by weight of acetylsalicylic acid, is between a minimum of about 0.1, preferably a minimum of about 0.3-0.5 and, in particular, a minimum of about 2, and a maximum of about 50, preferably a maximum of about 10. It is also possible by use of these experimental procedures to determine the optimal time interval between the administration of the xanthine derivative and of the acetylsalicylic acid, or the optimal rate of release from the pharmaceutical formulations. The xanthine derivative, for example pentoxifylline, is released first, and then, 15 minutes to 4 hours later, the acetylsalicylic acid component. A time interval of about 20 to 90 minutes, and especially between 30 and 60 minutes, is particularly preferred. Of course, the dose which is to be administered depends on a variety of factors, such as the organism to be treated (i.e. human or animal, age, weight and general state of health), the severity of the symptoms, the disease which is to be treated, (where present) the nature of the concurrent treatment with other medicaments, the frequency of treatment etc. The doses are generally administered up to five times a day, and preferably once to three times a day. The ratio by weight of individual active compounds should lie within the range indicated above, and the amount of the constituents should lie within the range indicated above, and the amount of the constituents should lie within the effective dose range which is tolerated by the organism which is to be treated.

For example, the preferred dose of acetylsalicylic acid is, when administered alone to humans, 500 to 2,000, in particular 1,000, mg two or three times a day. The preferred dose of pentoxifylline is, when administered alone to humans, 200 to 800, in particular 300 to 600, mg two or three times a day. It is possible to calculate exactly the relevant amounts from these ratios by weight for the ratio of acetylsalicylic acid to pentoxifylline. Thus, a suitable treatment comprises the administration of, for example, one, two or more, preferably 3 to 8, single doses of the combination products according to the invention, each containing 100 to 600, preferably at least 200 and, in particular, up to 400 mg of the xanthine derivative, in particular of pentoxifyllin, and 10 to 2,000, for example up to 400, mg of acetylsalicylic acid or the equivalent amount of a salt, where the amount is, of course, dependent on the number of single doses as well as the disorder which is to be treated, and a single dose can comprise, for example, several tablets which are administered simultaneously. However, the invention also allows good results to be obtained in cases in which the administration of particularly small amounts of acetylsalicylic acid (for example 10-50 mg per day or less) is desired, the results being considerably better than when the same amount of acetylsalicylic acid is administered alone.

The agents according to the invention can be used in the same manner as known antithrombotic agents and agents inhibiting blood platelet aggregation. In vivo uses comprise the administration to humans and animals in order to prevent the formation of arterial and venous blood clots, such as, for example, to prevent transient ischemic attacks, and for the long-term prophylaxis following myocardial infarctions and strokes, and for arteriosclerosis, as well as for treatment after surgery to prevent postoperative thrombosis and for the aftertreatment of cancer to prevent or reduce the metastatic effect. Administration to patients who are connected to heart-lung machines and to kidney dialysis is also possible, likewise to patients with artificial heart valves, vessel prostheses etc. Of course, administration for the actual indications for the individual constituents, for example promotion of blood flow (intermittent claudication) and analgesic and antiinflammatory effects (including for chronic inflammation) is possible. In antiinflammatory preparations the ratio of the xanthine derivative to component B is in general between 0.1 and 1, while it is in other preparations in general between 0.5 and 50.

In vivo investigations

The combination of pentoxifylline and acetylsalicylic acid was assessed in vivo using a design of experiment in which an intravascular thrombosis was generated with a laser in the arterioles of the mesentery of a rat. This procedure is a suitable experimental model for the combination product according to the invention. The evaluation was carried out by analysis by vital microscopy (Nature, 218 (1968) 887 and Haemostasis 13 (1983) 61 and IRCS Med. Sci. 12 (1984)91).

The test substances were administered in 0.9% sodium chloride solution (which contained 1% carboxymethylcellulose (Serva, Heidelberg)) either orally, intraperitoneally or intravenously. Control animals were treated in the corresponding manner but without the test substances. The experimental animals used were male or female Sprague-Dawley or Wistar rats.

The investigation with pentoxifylline, other xanthine derivatives and acetylsalicylic acid in the laser-induced thrombosis model was carried out on female Sprague-Dawley rats of body weight about 200 g. The animals which were to be investigated underwent s.c. premedication with 0.1 mg of atropine sulfate in solution and were anesthetized with 100 mg of ketamine hydrochloride and 4 mg of xylazine per kg of body weight i.p. The investigation made use of arterioles and venules of the mesentery, which was coated with degassed liquid paraffin, having a diameter of about 13 $\mu$m. The beam of a 4W argon laser (supplied by Spectra Physics, Darmstadt) was introduced coaxially, by means of a beam adaptation and adjustment system (supplied by BTG, Munich), into the inverted optical path of a microscope (ICM 405, LD-Epipland 40/0.60; supplied by Zeiss, Oberkochen). The wavelength used was 514.5 nm, with an energy above the objective of 30.5 mW. The exposure time per single shot was 1/15 sec. All the measuring operations were recorded by video camera (Trinicon tube, Sony, Cologne) and stored in a recorder (Sony, U-matic ¾"). The test substances were administered in various doses to the experimental animals, orally one hour, and on i.v. administration 10 min., before the start of the experiment, control animals receiving the same amount of placebo. The substances were administered as follows: 1) as a single dose, (2) together as a combination or (3) first acetylsalicylic acid and, after 1 h, pentoxifylline or another xanthine derivative, and (4) first pentoxifylline or another xanthine derivative and, after 1 h, acetylsalicylic acid (Table 1a). Table 1b shows the effect of various time intervals. Table 1c summarizes the effects of other xanthine derivatives.

Evaluation

The number of shots needed to induce a defined thrombus is counted. The shot frequency amounts to one lesion every 2 minutes, and all the thrombi with a minimum size of ¼ of the vessel radius which were formed during the observation period were counted and measured.

The results of the experiment were subjected to statistical analysis using the $^2$ test (L. Cavalli-Storza, Biometrie (Biostatistics), Stuttgart, 1969, pages 49 et seq.).

Results

The results are recorded in Tables 1a–c. The effects of the single oral doses of 5 mg/kg acetylsalicylic acid or pentoxifylline are not significant, but pentoxifylline does show 20% inhibition of thrombus formation. Both substance have a significant effect at an oral dose of 10 mg/kg. Simultaneous administration of pentoxifylline and acetylsalicylic acid produced no effect in the laser model. This was also the case when acetylsalicylic acid was administered first and pentoxifylline was administered after 1 h. In contrast, administration of pentoxifylline first and acetylsalicylic acid after 1 h has a dose-dependent, significant effect in the model of laser-induced thrombosis in the arteriles and venules of the rat mesentery. The superadditive effect of this sequential administration compared with single doses is clearly evident from the percentage change compared with controls (Table 1a).

The results listed in Table 1b show that there is a wide range for the timespan which can be selected between the two single doses, the optimum being between 15 and 180 minutes. The effects according to the invention can also be achieved with other xanthine derivatives (see patent claims) when they are administered with acetylsalicylic acid but displaced in time. The antithrombotic effects of a selection of these xanthine derivatives are recorded in Table 1c.

The sequential administration can be carried out using a commercially available perfusion unit with two separately controllable chambers (for example that supplied by Braun, Melsungen; with motor-driven feed designed to be separate via a timeswitch). The two chambers of the perfusion unit were filled with pentoxifylline solution (corresponding to 10 mg of pentoxifylline/kg rat) and with acetylsalicylic acid solution (corresponding to 1 mg/kg respectively (for solvent, see above). The timeswitch controlled the injection of the acetylsalicylic acid solution 20 min. after the injection of the pentoxifylline solution into the caudal vein. In a comparison experiment, both chambers were injected simultaneously. The results corresponded to the measurements obtained after oral administration, i.e. the effects obtained on sequential administration were far greater than those obtained on simultaneous administration.

Ex vivo investigations

Platelet aggregation was determined by procedures known per se. Male rabbits (own breed, BASK, SPF Wiga about 2.5 to 3.5 kg) were treated intravenously (ear vein) with pentoxifylline and/or DL-lysine monoacetylsalicylate dissolved in physiological saline. Then blood was taken from the ear vein, a 3.8% strength trisodium citrate solution was added in the ratio 9:1, and the mixture was incubated at room temperature for 45 minutes. It was subsequently centrifuged at 1,000 revolutions per minute for 10 minutes. The upper layer, which comprises the platelet rich plasma, was separated off, and the lower layer was centrifuged at 28,000 revolutions per minute for 10 minutes. The upper layer now contained the platelet-poor plasma, which was likewise separated off. The platelet-rich plasma was diluted with the platelet-poor plasma to about 6 to $7 \times 10^8$ platelets/ml (Coulter counter, Coulter Electronics, Krefeld). Platelet aggregation was followed optically by measurement of the light transmission in a Born aggregometer (supplied by Labor GmbH, Hamburg). The volume of the test mixture was 0.25 ml, and the temperature was 37° C. Aggregation was induced with $2 \times 10^{-4}$M arachidonic acid (Serva, Heidelberg) purified by preparative high-pressure liquid chromatography (HPLC reversed phase C-18 column under protective gas (argon). The increase in platelet aggregation was followed on the basis of the light transmission. The variable measured in this system is the maximum aggregation amplitude E. The results are recorded in Table 2.

Female rats (Hoe Wiskf, about 180 g) were treated by oral administration of the following medicaments (in polyethylene glycol (PEG), NW 400, corresponding to 1 ml/kg):

Experiment (1.) 30 mg/kg pentoxifylline, after 30 min 3 mg/kg acetylsalicylic acid.

Experiment (2.) 30 mg/kg pentoxifylline, after 30 min. 10 mg/kg acetylsalicylic acid.

Experiment (3.) 30 mg/kg acetylsalicylic acid, after 30 min. 30 mg/kg pentoxifylline.

Experiment (4.) 10 mg/kg acetylsalicylic acid, after 30 min. 30 mg/kg pentoxifylline.

Experiment (5.) 30 mg/kg pentoxifylline, after 30 min. only solvent. Control experiment (6.) ml/kg PEG 400 without medicaments.

These procedures were repeated after 18 hours and, 1 hour after the last administration, the rats were sacrificed under ether anesthesia, and the thoracic aorta was removed. Segments of aorta were immediately incubated in 3 ml of buffered 0.09M NaCl solution, pH=7.5, at 24° C. for 30 min. Aliquots of the supernatants from the aortas were then used as inhibitors of the aggregation of human platelets induced with adenosine diphosphate, as follows: blood was taken, by careful cannulation of the antecubital vein, from apparently healthy male and female volunteers who had taken no medicaments in the preceding 10-day period, and was immediately stabilized with sodium citrate (ad 0.38%). Platelet-rich plasma (PRP) was obtained as the supernatant after centrifugation at 140×g for 15 minutes, the platelet content in this being in the range $1.5-3.5 \times 10^8$/ml (Coulter counter). Platelet aggregation was followed optically by measurement of the light transmission in a Born aggregometer (supplied by Labor GmbH, Hamburg). The total volume of the test mixture was 0.25 ml. The plasma was pre-incubated with the aorta supernatants at 37° C. for 5 min., and then aggregation was induced with $2 \times 20^{-6}$M adenosine diphosphate. Dose-effect curves as a function of the weight of the aorta were constructed from the maximum aggregation applitudes in each case, and the antiaggregatory activity in the supernatant from 0.1 mg of aorta was determined from these graphs. The weights of the aortas were determined by weighing of the aortas which had been dried at 60° C. for 20 hours. The measurements of aggregation were carried out in the period 1-2 hours after the blood was taken.

Toxicity test. Method

Rats were treated orally as described above, but with increasing doses. One group received pentoxifylline, and a second group received pentoxifylline plus acetylsalicy-lic acid in the ratio by weight of 10:1. The lethal dose was calculated by the customary standard procedure (Litchfield and Wilcoxon, 1949) as the $LD_{50}$: $LD_{50}$ (pentoxifylline) = 1400 mg/kg $LD_{50}$ (pentoxifylline/acetylsalicylic acid) = 1400 mg/kg

Results

The toxicological tolerability was the same for both groups. This means that the ratio between the pharmaceutical dose and the lethal dose for the combination of pentoxifylline and acetylsalicylic acid according to the invention is much smaller, and thus is considerably more favorable, than on administration of pentoxifylline or acetylsalicylic acid alone.

Test of gastric tolerance

Method

Fasted male Sprague-Dawley rats weighing 200-300 g were treated orally as described above with pentoxifylline and, after one hour, with acetylsalicylic acid, or only with acetylsalicylic acid. 24 hours after the last medication, the stomach was cut open along the lesser curvature, cleaned under running water, and inspected for mucosal lesions. All lesions visible on macroscopic inspection of the mucosa of the glandular stomach were regarded as ulcers.

Result

The gastric ulcerogenicity of acetylsalicylic acid is unaffected by pretreatment with pentoxifylline (Table 4). This means that the ratio of the pharmaceutical dose to the dose which is not tolerated by the stomach for the combination according to the invention (administration of pentoxifylline before acetylsalicylic acid) is considerably smaller and more favorable than that on administration of acetylsalicylic acid alone since, according to Table 1, considerably larger amounts of acetylsalicylic acid are necessary to achieve the same amtithrombotic effects.

Investigation using a model of chronic inflammation

The hemorheological, antithrombotic, antiaggregatory and antiinflammatory effects of the combinations according to the invention were investigated after oral administration for 21 days in the pathological model of adjuvant arthritis (induced with Mycobacterium butyricum) in the rat by the method of Clinical Hemorheology 3 (1983) 469-480, and were compared with those of the appropriate individual substances. Blood was taken from the thoracic aorta 1 hour after the last administration of substance. All the details of the determination of the hemorheological effect were as described in Clinical Hemorheology 4 (1984) 263-273. The erythrocyte deformability was quantitatively determined in a filtrometer (Myreene MF 4, Roetgen, Germany) by evaluation of the initial gradient of the flow curve. Table 5a shows that the erythrocyte filterability, which is reduced in arthritic rats compared with healthy control rats, can be increased again by acetylsalicylic acid and pentoxifylline. Even combined administration of the two substances at the same time shows superadditive effects, but they are particularly promoted with consecutive administration (pentoxifylline 1 hour before acetylsalicylic acid).

The antithrombotic effect was measured using the laser model as described above. Table 5b shows the results. Whereas an average of 2.173 (=100%) laser shots had to be used to achieve a throbus in healthy control animals, 0.99 (=46%) shots are sufficient for arthritic animals, i.e. the tendency to thrombosis is increased in diseased animals. Table 5b shows that the tendency to thrombosis is decreased by treatment with the medicaments and, in particular, by administration of the combination according to the invention there is approximation to the figures found for healthy animals.

The measurements of platelet aggregation were carried out as described above in detail. However, instead of arachidonic acid 0.04 mg of collagen was used to induce platelet aggregation in 1 ml of platelet-rich plasma (PA II aggregometer from Myrenne, Roetgen). The aggregation amplitude (aggregation Tendency) is highest (=100%) for the untreated arthritic rats, while no aggregation occurs with 0.04 mg of collagen in healthy rats (Table 5c). The listed results show that the pathologically increased aggregation tendency in the arthritic rat can be reduced by the medicaments mentioned. Consecutive administration (pentoxifylline and, 1 hour later, acetylsalicylic acid) again shows superadditive effects.

The antiinflammatory effect was quantitatively measured, as quoted above, using the volume of the edema of the paw and using the standard necrosis index. The formation of necrosis and edema decreases markedly on treatment with the medicaments. Table 6 shows the relative improvement in the symptoms of the treated animals compared with the untreated arthritic rats. The consecutive administration according to the invention (pentoxifylline and, 1 hour later, acetylsalicylic acid) again shows superadditive effects.

Pharmaceutical formulations

It was also possible, in place of the i.v. injection by a perfusion unit described above, to use suspensions and solid formulations, which are suitable for oral, peroral and rectal administration, to achieve superadditive effects.

Examples of formulations of this type for administration to humans contain x mg of pentoxifylline or other xanthine derivatives (see Examples 1-17) as the pure substance and/or as a commercially available finished formulation (Trental®, supplied by Albert Roussel Pharma GmbH, Wiesbaden or Rentylin®, supplied by Dr. Rentschler Arzneimittel GmbH & Co., Lauphheim (abbreviated to T and R respectively) or parts of these finished formulations, combined with y mg of acetylsalicylic acid which can also be bound to basic ion exchangers (Dowex® 1×8, and QAE-Sephadex® (Serva, Heidelberg)) or to an adsorber resin (Amberlite® XAD 2), or can be in the form of commercially available microcapsules (Colfarit®, Bayer AG, Leverkusen (abbreviated to C)) or crystals (R 95D and M 80D supplied by Rohm Pharma GmbH, Weiterstadt, Germany). The pharmaceutical vehicles in these combinations are gels which have been solidified by heating:

(a) 20 percent by weight of gelatine/1 percent by weight of glycerine in water, and (b) 1 percent by weight of agarose in water, and (c) 10 percent by weight of ethylcellulose 150 (Hercules GmbH, Hamburg) in acetone/water (80:20% by weight), in each case with or without 8 percent by weight of pentoxifylline, or another xanthine derivative, stirred in, or commercially available gelatine capsules (for administration to humans and large animals, size D (supplied by Kapsugel, Basle)).

The pharmaceutical formulations (see Examples 1-17) are added to 10 ml of canine gastric juice or 10 ml of 0.1N HCL and are maintained at 37° C. in vitro, stirring gently. Aliquots of the supernatant are taken at specified time intervals and are fractionated by high-pressure liquid chromatography (column: Rad Pak C18 (Waters GmbH, Eschborn, Germany) 100×8 mm, 10 $\mu$m, mobile phase: 300 ml of methanol/1 ml of acetic acid, 700 ml of water, flow rate: 1.5 ml/min) and the components are determined quantitatively by UV detection at 280 nm. The pharmaceutical formulations are inserted in duodenal fluid (dog) or sodium bicarbonate solution (pH=7.4) in an analogous manner.

For administration to small animals (see Table 1, rats), the constituents of the formulations mentioned in Examples 1-17 are each reduced to 1/200 of the weights, or capsules of sizes 4 and 5 are used.

| Example No. | Pharmaceutical vehicle | Content of acetyl-salicylic acid | Content of xanthine derivative (total) | released after (...min) at pH = 1.8 | |
|---|---|---|---|---|---|
| | | | | % acetylsalicylic acid | % xanthine derivative |
| 1 | Capsule | 58 mg (M80D) | 350 mg 7-(2-Oxopropyl)-1,3-di-n-butyl-xanthine | 0 (15)<br>0 (30)<br>2 (90) (x) | 77 (15)<br>99 (30) |
| 2 | Capsule | 33 mg (M80D) | 100 mg 1-Hexyl-3,7-dimethyl-xanthine | 0 (15)<br>0 (30) (x) | 79 (15)<br>98 (30) |
| 3 | Capsule | 45 mg (M80D) | 400 mg pentoxifylline | 0 (15)<br>0 (30) (x) | 79 (15)<br>99 (30) |
| 4 | Coating: gelatine containing 205 mg xanthine<br>Core: C | 500 mg (C) | 205 mg 1-(5-Hydroxyhexyl)-3,7-dimethyl-xanthine | 0 (5)<br>0 (10)<br>2,6 (15) | 2,5 (5)<br>15 (10)<br>28 (15) |
| 5 | Coating: gelatine containing 195 mg xanthine<br>Core: R 95 D | 105 mg (R95D) | 195 mg 1-(5-Hydroxyhexyl)-3,7-dimethylxanthine | 0 (5)<br>0 (10)<br>4 (15)<br>22 (60) | 6 (5)<br>21 (10)<br>35 (15)<br>76 (60) |
| 6 | 1st Layer: 1 g gelatine containing M80D<br>2nd Layer: R | 408 mg (M80D) | 400 mg pentoxifylline | 0 (15)<br>0 (30)<br>0 (60) (x) | 10 (15)<br>20 (30)<br>40 (60) |
| 7 | 1st Layer: agarose, containing 70 mg xanthine plus M80D<br>2nd Layer: R | 85 mg (M80D) | 470 mg pentoxifylline | 0 (60) (x) | 30 (60) |
| 8 | Coating: agarose, containing 190 mg xanthine<br>Core: Acetylsalicylic acid bound to Dowex | 62 mg (Dowex 1 × 8) | 190 mg 1-(5-Hydroxyhexyl)-3-Methyl-7-propyl-xanthine | 0 (5)<br>0 (10)<br>3 (15) | 4 (5)<br>18 (10)<br>31 (15) |
| 9 | Coating: gelatine containing 280 mg xanthine<br>Core: Acetylsalicylic acid | 30 mg. | 280 mg 1-(5-Oxohexyl)-3-methyl-7-propyl-xanthine | 0 (5)<br>5 (10)<br>30 (15) | 3 (5)<br>18 (10)<br>35 (15) |
| 10 | Suspension of 1 ml xanthine solution (50 mg/ml) and M80D | 530 mg (M80D) | 50 mg 1,3-Dimethyl-7-(5-hydroxyhexyl)-xanthine | 0 (5)<br>0 (15)<br>2 (20) | 4 (5)<br>20 (15)<br>35 (20) |
| 11 | Coating: gelatine containing 100 mg xanthine<br>Core: Acetylsalicylic acid bound to Amberlite | 95 mg (Amberlite) | 100 mg 1,3-Dimethyl-7-(5-oxohexyl)-xanthine | 0 (5)<br>0 (15)<br>2 (20) | 4 (5)<br>20 (15)<br>35 (20) |
| 12 | Capsule | 390 mg (M80D) | 180 mg pentoxifylline | 0 (15)<br>0 (30)<br>0 (60)<br>0 (90) (x) | 10 (15)<br>20 (30)<br>38 (60)<br>46 (90) |
| 13 | Coating: gelatine containing 65 mg pentoxifylline and 100 mg M80D | 108 mg (M80D) | 465 mg pentoxifylline | 0 (60) (x) | 18 (60) |

-continued

| Example No. | Pharmaceutical vehicle | Content of acetyl-salicylic acid | Content of xanthine derivative (total) | released after (... min) at pH = 1.8 % acetylsalicylic acid | % xanthine derivative |
|---|---|---|---|---|---|
| 14 | Core : pentoxifylline (T) Capsule | 35 mg (M80D) | 200 mg pentoxifylline(T) 60 mg pentoxifylline | 0 (30) 0 (60) (x) | 28 (30) 39 (60) |
| 15 | Capsule | 62 mg (M80D) | 200 mg pentoxifylline(T) | 0 (30) 0 (60) 0 (75) (x) | 19 (30) 29 (60) 36 (75) |
| 16 | 1st Layer: pent-oxifylline(R) 2nd Layer: 1 g Agarose,containing M80D | 82 mg (M80D) | 400 mg pentoxifylline | 0 (30) 0 (60) (x) | 20 (30) 38 (60) |
| 17 | 1st Layer: Pent-oxifylline(R) 2nd Layer: Gelatine, containing 190 mg Pentoxifylline and M80D | 11 mg (M80D) | 590 mg pentoxifylline | 0 (30) 0 (60) (x) | 32 (30) 39 (60) |

(x)The M80D acetylsalicylic acid crystals which are insoluble in gastric acid are quantitatively dissolved at pH 7.4.

TABLE 1a

Effect of various sequences of administration of pentoxifylline and/or acetylsalicylic acid on Laser-induced thrombosis

| Substance | Dose mg/kg rat weight oral | Number of animals n | Number of lesions/animal | Number of shots $\bar{x}$ | SEM | Changes from controls absolute | % | $\chi^2$ test |
|---|---|---|---|---|---|---|---|---|
| Control | — | 12 | 48 | 2,17 | 0,01 | — | — | — |
| Acetylsalicylic acid | 1 | 6 | 24 | 1,88 | 0,35 | −0,35 | −13 | |
| Acetylsalicylic acid | 5 | 6 | 24 | 1,79 | 0,20 | −0,38 | −18 | |
| Acetylsalicylic acid | 10 | 6 | 24 | 2,92 | 0,20 | 0,75 | 35 | p < 0,01 |
| Pentoxifylline | 5 | 6 | 24 | 2,63 | 0,24 | 0,46 | 21 | |
| Pentoxifylline | 10 | 6 | 24 | 3,33 | 0,36 | 1,16 | 54 | p < 0,01 |
| Pentoxifylline + Acetylsalicylic acid | 5 +5 | 6 | 24 | 2,42 | 0,26 | 0,25 | 12 | |
| Pentoxifylline + Acetylsalicylic acid | 10 +1 | 6 | 23 | 2,52 | 0,26 | 0,35 | 16 | |
| Pentoxifylline + Acetylsalicylic acid | 10 +10 | 6 | 24 | 2,25 | 0,26 | 0,08 | 4 | |
| Acetylsalicylic acid after 1 h pentoxifylline | 5 +5 | 6 | 24 | 1.96 | 0,19 | −0,21 | −10 | |
| Acetylsalicylic acid after 1 h pentoxifylline | 1 +10 | 7 | 28 | 2.36 | 0,23 | 0,19 | 9 | |
| Acetylsalicylic acid after 1 h pentoxifylline | 10 +10 | 6 | 24 | 2.17 | 0,21 | 0 | 0 | |
| Pentoxifylline after 1 h acetylsalicylic acid | 5 +5 | 6 | 24 | 3,21 | 0,21 | 1,04 | 48 | p < 0,01 |
| Pentoxifylline after 1 h acetylsalicylic acid | 10 +1 | 6 | 24 | 3,88 | 0,33 | 1,71 | 79 | p < 0,01 |
| Pentoxifylline after 1 h acetylsalicylic acid | 10 +10 | 6 | 24 | 4,71 | 0,35 | 2,54 | 117 | p < 0,01 |
| Pentoxifylline | 30 | 6 | 24 | 3,97 | 0,34 | 1,8 | 83 | |
| Acetylisalicylic acid | 30 | 6 | 24 | 3,21 | 0,2 | 1,04 | 48 | |
| Pentoxifylline after 1 h acetylsalicylic acid | 30 +1 | 6 | 24 | 4,86 | 0,34 | 2,69 | 124 | p < 0,01 |
| Pentoxifylline after 1 h acetylsalicylic acid | 30 +10 | 6 | 24 | 4,83 | 0,37 | 2,66 | 123 | p < 0,01 |
| Acetylsalicylic acid (Sephadex ®) | 2 | 6 | 24 | 2,50 | 0,27 | 0,33 | 15 | |
| Pentoxifylline + after 1 h acetylsalicylic (Sephadex ®) | 10 +2 | 6 | 24 | 3,95 | 0,32 | 1,78 | 82 | p < 0,01 |
| Formulation analogous to Example 3, acid-insoluble microencapsulated acetylsalicylic acid (M80D) | 10 | 6 | 24 | 2,79 | 0,19 | 0,62 | 29 | |
| Pentoxifylline + acid-insoluble microencapsulated acetyl-salicylic acid (M80D) | 10 +10 | 6 | 24 | 4,28 | 0,32 | 2,11 | 97 | p < 0,01 |
| Formulation analogous | 10 | 6 | 24 | 2,78 | 0,20 | 0,63 | 29 | |

TABLE 1a-continued

Effect of various sequences of administration of pentoxifylline and/or acetylsalicylic acid on Laser-induced thrombosis

| Substance | Dose mg/kg rat weight oral | Number of animals n | Number of lesions/animal | Number of shots x | SEM | Changes from controls absolute | % | $\chi^2$ test |
|---|---|---|---|---|---|---|---|---|
| to Example 16 Acid-insoluble microencapsulated acetylsalicylic acid (M80D) Pentoxifylline + acid-insoluble microencapsulated acetylsalicylic acid (M80D) | 10 30 | 6 | 24 | 4,88 | 0,35 | 2,71 | 125 | $p < 0,01$ |

TABLE 1b

Effect of pentoxifylline and acetylsalicylic acid on laser-induced thrombosis.
Effect of the time interval between the administrations of the substances.
Dose in each case 10 mg/kg pentoxifylline orally then, after the time indicated, 1 mg/kg acetylsalicylic acid

| Substance | Number of animals | Number of lesions | $\bar{x}$ | SEM | % change from controls | $\chi^2$-Test |
|---|---|---|---|---|---|---|
| Control (Placebo) | 8 | 32 | 2,19 | 0,02 | — | — |
| Pentoxifylline without acetylsalicylic acid | 9 | 36 | 3,27 | 0,32 | +49 | $p < 0,05$ |
| Acetylsalicylic acid without pentoxifylline | 9 | 36 | 1,90 | 0,34 | −13 | |
| 0 min | 9 | 36 | 2,18 | 0,13 | 0 | — |
| 15 min | 5 | 20 | 3,42 | 0,21 | +56 | $p < 0,05$ |
| 30 min | 5 | 20 | 3,59 | 0,17 | +64 | $p < 0,01$ |
| 45 min | 5 | 20 | 3,68 | 0,19 | +69 | $p < 0,01$ |
| 60 min | 7 | 28 | 3,71 | 0,18 | +76 | $p < 0,01$ |
| 90 min | 4 | 16 | 3,33 | 0,23 | +52 | $p < 0,01$ |
| 120 min | 4 | 16 | 2,91 | 0,21 | +33 | $p < 0,01$ |
| 180 min | 8 | 32 | 2,63 | 0,21 | +20 | $p < 0,05$ |
| 300 min | 8 | 32 | 2,25 | 0,17 | +3 | — |

TABLE 1c

Antithrombotic effect of xanthine derivatives (in each case 10 mg/kg orally, n = 3) (column a) or consecutive administration according to the invention (10 mg/kg xanthine derivative and, 1 hour later, 1 mg/kg acetylsalicylic acid orally, n = 3) (column b) in the laser model on the rat. The percentage improvement compared with the placebo controls is shown. Experimental details in the text.

| Substance | a | b |
|---|---|---|
| Control (only acetylsalicylic acid) | — | −10% |
| 1-(5-Oxohexyl)-3-methyl-7-propylxanthine | 42% | 56% |
| 1-(5-Hydroxyhexyl)-3-methyl-7-propylxanthine | 40% | 53% |
| 1-(5-Hydroxyhexyl)-3,7-dimethyl-xanthine | 52% | 68% |
| 1-Propyl-3-methyl-7-(5-hydroxyhexyl-)-xanthine | 35% | 42% |
| 1-Hexyl-3,7-dimethylxanthine | 39% | 46% |
| 1-Ethyl-3-ethyl-7-(5-oxohexyl-)-xanthine | 41% | 48% |
| 1-n-Butyl-3-n-butyl-7-(2-oxopropyl-)-xanthine | 33% | 50% |
| 1-(5-Hydroxyhexyl)-3-methyl-7-(2-methylpropyl)-xanthine | 23% | 34% |
| 1-(2-Methylpropyl)-3-methyl-7-(5-oxohexyl-)-xanthine | 28% | 39% |
| 1-(5-Oxohexyl)-3-methyl-7-(2-methylpropyl)-xanthine | 28% | 39% |
| 1-(2-Methylpropyl)-3-methyl-7-(5-hydroxyhexyl)-xanthine | 29% | 39% |
| 1-(Isopropyl)-3-methyl-7-(5-hydroxyhexyl-)-xanthine | 31% | 36% |
| 1-(3-Methylbutyl)-3-methyl-7-(5-oxohexyl)-xanthine | 26% | 35% |
| 1-(3-Methylbutyl)-3-methyl-7-(5-hydroxyhexyl)-xanthine | 28% | 37% |
| 1-(3-Oxobutyl)-3-methyl-7-propyl-xanthine | 40% | 49% |

TABLE 2

Time course of the effect of pentoxifylline and/or DL-lysine monoacetylsalicylate on platelet aggregation

| | Substance | Time course (min) | i.v. dose mg/kg | Aggregation amplitude E ex vivo |
|---|---|---|---|---|
| I. | without control | 0 | — | 27,5 |
| | DL-Lysine monoacetylsalicylate | 15 | 1,5 | |
| | | 30 | | 23,5 |
| | DL-Lysine monoacetylsalicylate | 35 | 0,5 | |
| | | 45 | | 19,5 |
| | Pentoxifylline | 90 | 20 | |
| | | 150 | | 20 |
| II. | without control | 0 | — | 26 |
| | Pentoxifylline | 15 | 20 | |
| | DL-Lysine monoacetylsalicylate | 45 | 1,5 | |
| | | 110 | | 0,5 |
| III. | without control | 0 | — | 23 |
| | Pentoxifylline | 15 | 10 | |
| | | 45 | | 22 |
| | Pentoxifylline | 60 | 10 | |
| | | 120 | | 20 |

TABLE 3

| Exeriment | 1 | 2 | 3 | 4 | 5 | 6 |
| --- | --- | --- | --- | --- | --- | --- |
| Aggregation amplitude E ($\times 10^2$) | 0,15 | 0,6 | 0,15 | 0,6 | 0,15 | 0,45 |
| Difference from the control experiment | −0,3 | +0,15 | −0,3 | +0,15 | −0,3 | — |

TABLE 4

Ulcerogenic effect of medicaments

| Substance | Acetylsalicylic acid mg/kg oral | Number of animals n | Number of animals with ulcers n |
| --- | --- | --- | --- |
| Acetyl-salicylic acid | 1,25 | 10 | 1 |
| | 12,50 | 10 | 2 |
| | 25 | 10 | 5 |
| | 50 | 10 | 7 |
| | 100 | 10 | 9 |
| Consecutive administration, i.e. in each case 100 mg/kg of pentoxyfylline 1 h before acetyl-salicylic acid | 1,25 | 10 | 1 |
| | 12,5 | 10 | 2 |
| | 25 | 10 | 5 |
| | 50 | 10 | 7 |
| | 100 | 10 | 8 |

TABLE 5

Effect of various medicaments on blood parameters of the arthritic rat (n = 8 per group) (for details, see text)

| Arthritic rat | erythrocyte filterability | tendency to thrombosis (number of shots) | induc. platelet aggregation |
| --- | --- | --- | --- |
| untreated | 59% | 46% | 100% |
| 10 mg Acetylsalicylic acid | 63% | 47% | 62% |
| 180 mg Acetylsalicylic acid | 68% | 91% | 35% |
| 30 mg Pentoxifylline | 79% | 87% | 94% |
| 30 mg Pentoxifylline-at the same time 10 mg Acetylsalicylic acid | 84% | 57% | 93% |
| 30 mg Pentoxifylline-at the same time 180 mg Acetylsalicylic acid | 86% | 91% | 43% |
| 30 mg Pentoxifylline, after 1 hour 10 mg Acetylsalicylic acid | 90% | 109% | 22% |
| 30 mg Pentoxifylline, after 1 hour 180 mg Acetylsalicylic acid | 96% | 104% | 30,5% |
| (healthy control rats | 100% | 100% | 0%) |

TABLE 6

Percentage improvement, compared with untreated arthritic rats, in the arthritic rats treated with various medicaments (n = 8 per group) (for details, see text).

| | Volume of paw edema | | Necrosis index |
| --- | --- | --- | --- |
| | left paw | right paw | |
| 10 mg Acetylsalicylic acid | 2 | 3 | 8 |
| 180 mg Acetylsalicylic acid | 28 | 26 | 28 |
| 30 mg Pentoxifylline | 3 | 0 | 7 |
| 30 mg Pentoxifylline 10 mg Acetylsalicylic acid | 3 | 0 | 4 |
| 30 mg Pentoxifylline/ 180 mg Acetylsalicylic acid | 10 | 13 | 28 |
| 30 mg Pentoxifylline/ after 1 hour 10 mg Acetylsalicylic acid | 9 | 12 | 19 |
| 30 mg Pentoxifylline/ after 1 hour 180 mg Acetylsalicylic acid | 34 | 32 | 34 |

We claim:

1. A method of treating inflammation in a host which consists of administering to the host an effective amount of a pharmaceutical consisting essentially of pentoxifylline or the salt thereof for said treatment.

* * * * *